US00PP18709P3

(12) United States Plant Patent
Conibear

(10) Patent No.: US PP18,709 P3
(45) Date of Patent: Apr. 1, 2008

(54) ***LUPINUS* PLANT NAMED 'RED RUM'**

(50) Latin Name: *Lupinus hybridus*
Varietal Denomination: Red Rum

(76) Inventor: Sarah Frances Conibear, West Country Nurseries Donkey Meadow, Woolsery, Bideford, Devon EX39 5QH (GB)

( * ) Notice: Subject to any disclaimer, the term of this patent is extended or adjusted under 35 U.S.C. 154(b) by 0 days.

(21) Appl. No.: 11/474,102

(22) Filed: Jun. 23, 2006

(65) Prior Publication Data

US 2007/0300345 P1 Dec. 27, 2007

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

USDA Plants Database for Lupinus hybridus Lem. [online], [retreived on Jul. 23, 2007]Retreived from the Internet <http://plants.usda.gov/java/jsp/classification/classification_print_friendly.jsp?fileNamePF=cl. . . >one page.*

* cited by examiner

*Primary Examiner*—Kent Bell
*Assistant Examiner*—June Hwu
(74) *Attorney, Agent, or Firm*—The Webb Law Firm

(57) ABSTRACT

'Red Rum' is a new variety of *Lupinus hybridus* that exhibits numerous and large-shaped red-colored flowers.

2 Drawing Sheets

Botanical classification: *Lupinus hybridus*.
Varietal denomination: 'Red Rum'.

BACKGROUND OF THE INVENTION

The present invention comprises a new and distinct cultivar of *Lupinus hybridus* known by the varietal name 'Red Rum'. The new variety was developed in Great Britain. The new variety is a result of cross breeding Russell Hybrid *Lupinus* Seedling #WCL 027/96 (female parent) (unpatented) and an unknown *Lupinus* male parent (unpatented). The purpose of the breeding program was to develop a cultivar that exhibited improved color, habit, and bloom form from other *Lupinus* varieties known to the breeder. The new variety is similar in growth habit to its female parent, but differs in flower color. The new variety is similar in flower color to *Lupinus hybridus* 'My Castle', but differs in flower size, growth habit, and the closeness of the flowers packed on a spike. The new variety was first asexually reproduced by basal cuttings/tissue culture in Great Britain. The new variety has been trial and field tested and has been found to retain its distinctive characteristics and remain true to type through successive asexual propagations. Characteristics that distinguish the new variety from others known to the breeder include:

- Clear and intense flower color;
- Flower form — papilionaceous, with large flowers packed closely on the flower spike; and
- Vigorous growth habit.

The new variety was grown in open soil with additional organic fertilizer applied. The new variety initiates and develops roots in 21 days at 15° C. A finished and flowering plant is produced in 36 weeks in a 21 cm container. The new variety exhibits sparse, but thick roots, that exhibit some branching.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
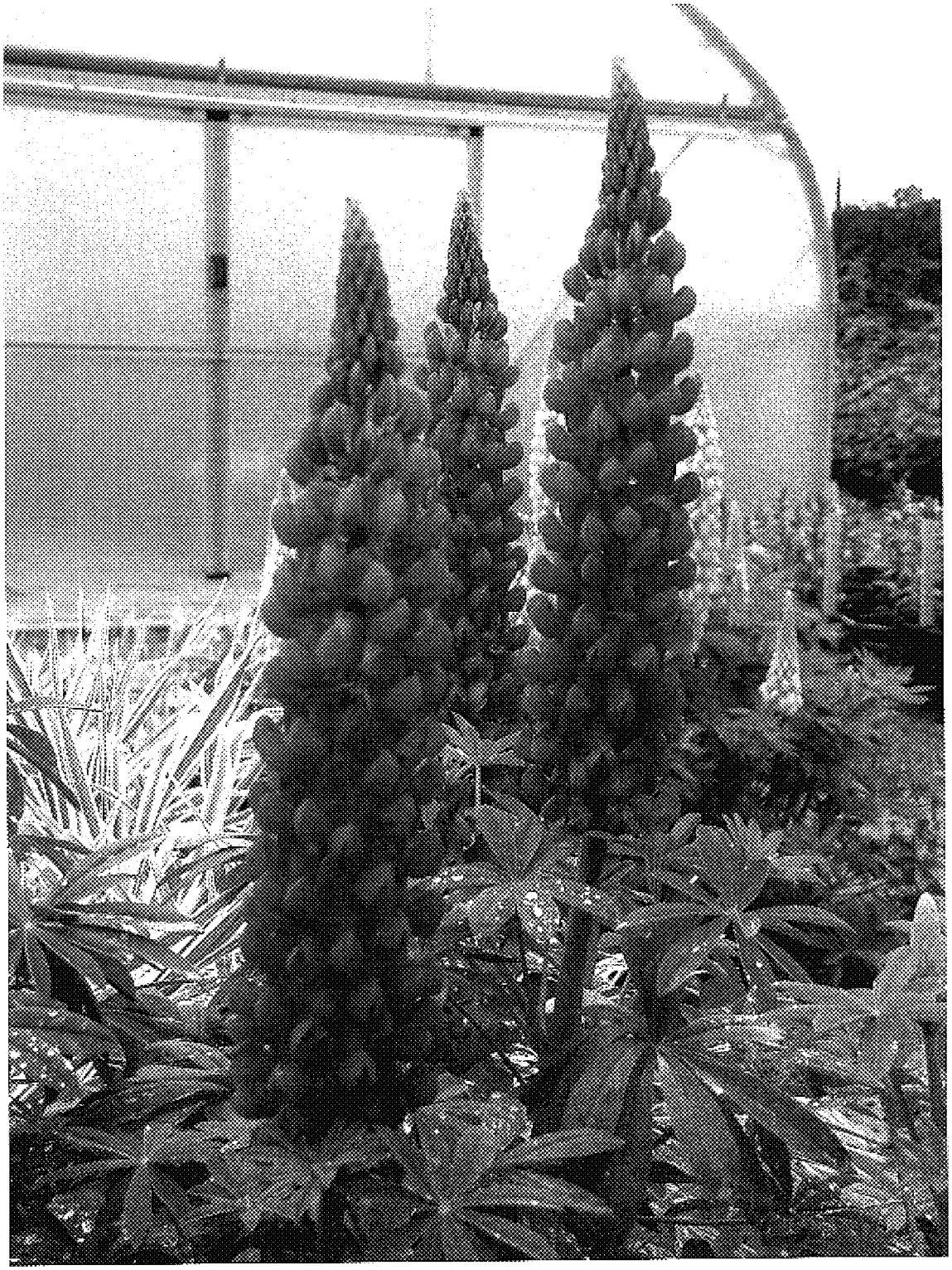
FIG. 1 is a photographic image of multiple plants of the new variety.
Figure 2:
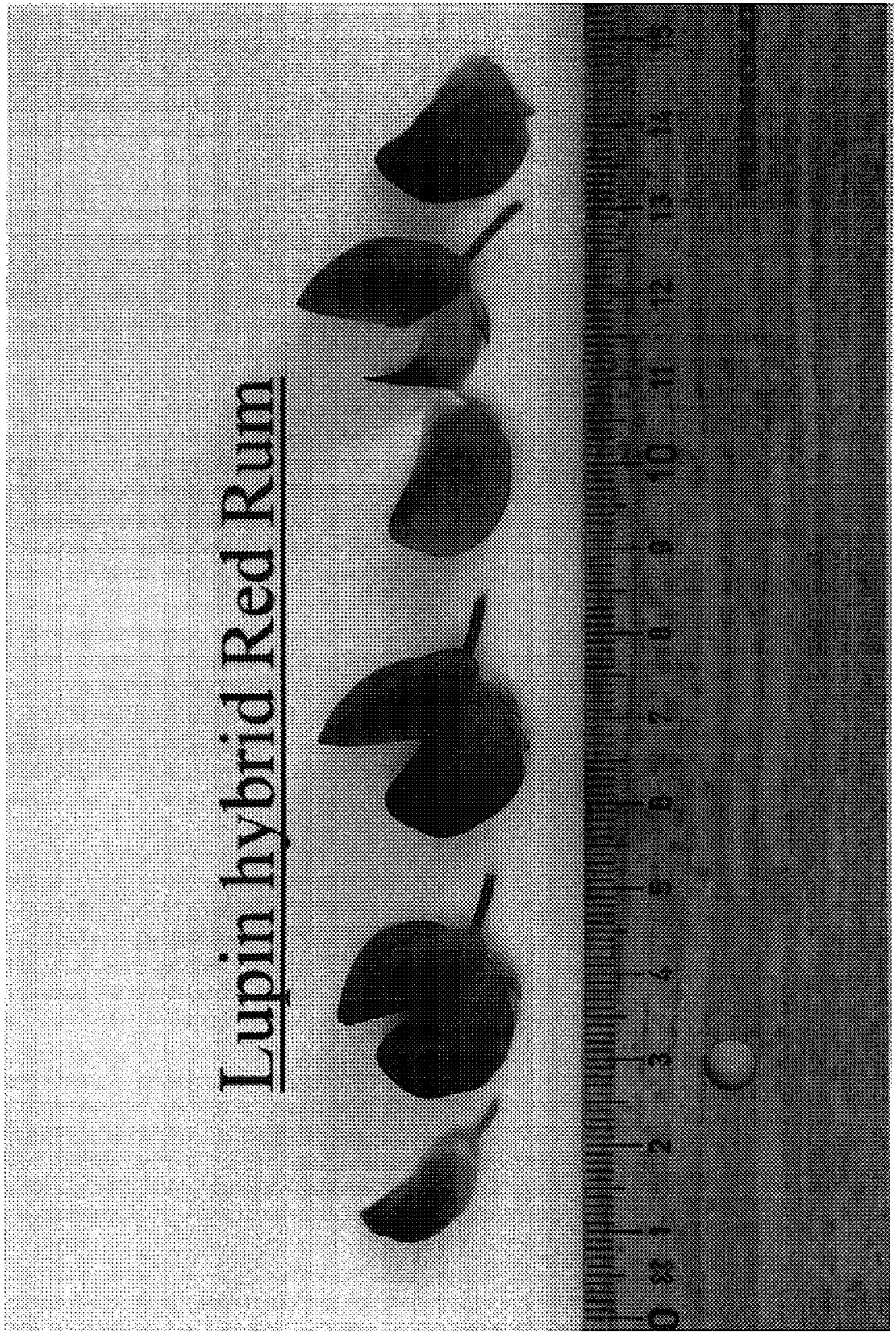
FIG. 2 is a close-up photograph of the petals of the new variety.

The following detailed description sets forth the characteristics of the new cultivar. The data which defines these characteristics were collected by asexual reproductions carried out in Great Britain. The color readings were taken outside under natural daylight. Color references are primarily to the R.H.S. Colour Chart of The Royal Horticultural Society of London.

PLANT

Form: Mounded and symmetrical.
Stem:
- *Diameter.*—12 mm.
- *Color.*—Between 144A and 144B, flushed with 70A.
- *Texture.*—Slightly hirsute, smooth with longitudinal ridges.
- *Pubescence.*—Slight to medium.

Height: 85 cm.
Vigor: Good.
Branching habit: Free.
Lateral branches:
- *Diameter.*—8 mm.
- *Internode length.*—4.2 cm.
- *Texture.*—Lightly hirsute, smooth with longitudinal ridges.
- *Pubescence.*—Present.
- *Color.*—144A and 144B, flushed with 70A.

Foliage:
- *Arrangement.*—Ascending spiral.
- *Length of leaf stalk.*—Basal foliage: 25 cm. Stem foliage; 19 cm.

*Size of leaf* (*overall*).—Length: 14.5 cm. Width: 14 cm.

*Leaflets.*—Shape of leaflet: Oblanceolate. Number: 13. Width: 2.2 cm. Length: 7.8 cm. Shape of apex: Acute. Shape of base: Cuneate. Aspect: Horizontal presentation. Margin type: Smooth; entire. Pubescence: Upper surface: None present. Lower surface: Slight. Color: Young leaflet: Upper surface: 137B. Lower surface: Varies between 137B and 137C. Mature leaflet: Upper surface: 137A. Lower surface: 137C. Petiole: Shape: Flattened and round. Length: Basal leaf: 25 cm. Stem Leaf: 19 cm. Diameter: 5 mm. Color: 144A. Venation: Central; mid-rib; colored the same as the leaflets.

FLOWER

Bud (described when buds where just beginning to open):

*Shape.*—Napiform.

*Diameter.*—8 mm.

*Length.*—16 mm.

*Color.*—61B and 67A.

Natural flowering season: May through July in The Netherlands.

Flower type and habit: Spike.

*Number of flowers per spike.*—155.

*Length of spike.*—44 cm.

*Diameter of spike.*—11.6 cm.

Corolla:

*Form.*—Zygomorphic.

*Petals.*—Standard Petals: Number: 2-fused. Length: 20 mm. Width: 10 mm. Shape: Ovate. Aspect: Parallel to spike. Margin: Smooth and entire. Wing Petals: Number: 2 Length: 20 mm. Width: 15 mm. Shape: Ovoid to kidney-shaped. Aspect: Tilted upward. Margin: Smooth and entire. Keel Petals: Number: 2-fused. Length: 17 mm. Width: 7 mm. Shape: Lingulate. Aspect: Located within wing petals and pointing upwards. Margin: Smooth and entire. Texture and appearance: Smooth and satin-like. Color: When opening (Standard Petals): Upper surface: 35A in the center; between 67B and 67C in the middle; 39C at the edge. Lower surface: 67A and 39A. Fully opened (Standard Petals): Upper surface: 49B in the center; between 67B and 67C in the middle; 39B at the edge. Lower surface: 67A and 39A. When opening (Wing Petals): Upper surface: 50A. Lower surface: 51B. Fully opened (Wing Petals): Upper surface: 50A. Lower surface: 51B. When opening (Keel Petals): Both surfaces: 39C and flushed with 39A. Fully opened (Keel Petals): Both surfaces: 39C and flushed with 39A. Keel tip color: 187A.

*Throat* (*visible when the standard petals are parted from the keel petals*).—Color: 4D. Texture: Smooth.

Calyx:

*Form.*—Two unequal halves.

*Length.*—7 mm.

*Diameter.*—12 mm.

*Sepal shape.*—Elliptical.

*Sepal margin.*—Smooth and entire.

*Sepal texture.*—Smooth with slight pubescence.

*Sepal size.*—Length: 7 mm. Width: 5 mm.

*Sepal color.*—Upper surface: 149C. Lower surface: Varies between 149C and 149D.

Fragrance: Slight.

Disease resistance/susceptibility: Susceptible to powdery mildew.

Texture tolerance: Medium to good.

Lasting quality: Medium to good.

REPRODUCTIVE ORGANS

Stamens:

*Number* (*per flower*).—There are two groups. A first group with 6 stamens and a second group with 4 stamens.

*Filaments.*—Length: First group: 4 mm. Second group: 6 mm. Fused: Yes.

*Anthers.*—Shape: First group: Pencil-like. Second group: Arrow-like. Length: First group: 2 mm. Second group: 1 mm. Color: First group: 169B. Second group: 25B.

*Pollen.*—Color: Varies between 25A and 25B. Amount: Plentiful.

*Pistils.*—Length: 9 mm.

*Style.*—Length: 9 mm. Color: 150C.

*Stigma.*—Shape: Spherical. Color: 150C.

Seed/Fruit production:

*Description of conditions when produced.*—Produced freely.

*Color.*—165A.

*Size.*—1.0 mm.

*Number.*—Approximately 2000 per plant.

I claim:

1. A new and distinct variety of *Lupinus hybridus* plant named 'Red Rum' as is herein described and illustrated.

* * * * *